United States Patent
Swiderski et al.

(10) Patent No.: US 11,273,162 B2
(45) Date of Patent: Mar. 15, 2022

(54) COMPOSITIONS AND METHODS TARGETING HCN CHANNELS FOR BREATHING THERAPEUTICS

(71) Applicants: Cyprianna Swiderski, Starkville, MS (US); Courtney Hunter, Jackson, MS (US)

(72) Inventors: Cyprianna Swiderski, Starkville, MS (US); Courtney Hunter, Jackson, MS (US)

(73) Assignee: Mississippi State University, Starkville, MS (US)

( * ) Notice: Subject to any disclaimer, the term of this patent is extended or adjusted under 35 U.S.C. 154(b) by 16 days.

(21) Appl. No.: 16/089,795

(22) PCT Filed: Apr. 3, 2017

(86) PCT No.: PCT/US2017/025789
§ 371 (c)(1),
(2) Date: Sep. 28, 2018

(87) PCT Pub. No.: WO2017/173458
PCT Pub. Date: Oct. 5, 2017

(65) Prior Publication Data
US 2019/0111061 A1    Apr. 18, 2019

Related U.S. Application Data

(60) Provisional application No. 62/317,114, filed on Apr. 1, 2016.

(51) Int. Cl.
*A61K 31/55* (2006.01)
*C07K 14/705* (2006.01)
*A61P 11/06* (2006.01)
*A61K 45/06* (2006.01)

(52) U.S. Cl.
CPC ............. *A61K 31/55* (2013.01); *A61K 45/06* (2013.01); *A61P 11/06* (2018.01); *C07K 14/705* (2013.01)

(58) Field of Classification Search
CPC ................... A61K 31/55; A61P 11/06
See application file for complete search history.

(56) References Cited

U.S. PATENT DOCUMENTS

| 7,361,649 B2 * | 4/2008 | Horvath | A61P 9/06 514/212.07 |
| 7,361,650 B2 * | 4/2008 | Horvath | C07D 223/16 514/212.07 |
| 2008/0066741 A1 | 3/2008 | Lemahieu et al. | |
| 2008/0153803 A1 | 6/2008 | Horvath et al. | |
| 2010/0041640 A1 | 2/2010 | Horvath et al. | |
| 2014/0171415 A1 | 6/2014 | Kley et al. | |

FOREIGN PATENT DOCUMENTS

| RU | 2383345 C1 | 3/2010 |
| WO | 2009158005 A1 | 12/2009 |

OTHER PUBLICATIONS

Legge et al., "Comparison of Two Oral Selective β2-Adrenergic Stimulant Drugs in Bronchial Asthma", British Medical Journal, vol. 1, No. 5750, pp. 637-639 (1971).*
Boschetto et al., "Link between chronic obstructive pulmonary disease and coronary artery disease: implication for clinical practice," Respirology, Apr. 30, 2012, vol. 17, No. 3, pp. 422-431.
Murphy et al., "Methylomic markers of persistent childhood asthma: a longitudinal study of asthma-discordant monozygotic twins," Clinical Epigenetics, Dec. 18, 2015, vol. 7, pp. 1-13.

* cited by examiner

*Primary Examiner* — Kevin E Weddington
(74) *Attorney, Agent, or Firm* — Butler Snow LLP (57) ABSTRACT

An object of the present invention to provide therapeutic compositions and methods for the prevention and/or treatment of airway obstructive disorders that involve bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. Compositions and methods for targeting HCN channels in airway smooth muscle to treat and/or prevent asthma and asthma-like conditions are disclosed. The compositions and methods include administering a therapeutically effective amount of HCN channel blocker, preferably ivabradine hydrochloride, to a subject in need thereof.

12 Claims, 1 Drawing Sheet

COMPOSITIONS AND METHODS TARGETING HCN CHANNELS FOR BREATHING THERAPEUTICS

CROSS-REFERENCE TO RELATED APPLICATIONS

This application claims priority to U.S. Provisional Application No. 62/317,114 to Cyprianna Swiderski and Courtney Hunter filed on Apr. 1, 2016, the contents of which are incorporated herein by reference in its entirety.

STATEMENT OF GOVERNMENT SUPPORT

This invention was made with government support under 0221637 awarded by the National Institute of Food and Agriculture (NIFA), USDA. The government has certain rights in the invention.

FIELD OF THE INVENTION

The present invention is generally directed toward therapeutic compositions and methods for targeting HCN channels in airway or bronchial smooth muscle, and more particularly in therapeutic compositions and methods of treating and/or preventing asthma and asthma-like conditions in a subject in need thereof by targeting HCN channels with therapeutic compositions.

BACKGROUND OF THE INVENTION

Bronchial hyper-responsiveness (BHR) is a defining asthma criterion impacted by bronchial smooth muscle (BSM) excitability.[1] Decreasing BHR in asthmatics decreases asthma severity, making it a pharmacologic goal in developing asthma therapeutics[3]. Hyperpolarization Activated Cyclic Nucleotide-Gated (HCN) channels generate hyperpolarizing ('funny') current ($I_f$) that regulates membrane excitability in cardiac muscle and nerves[4], and in association with smooth muscle in certain organs systems[5-8]. The role of HCN channels in bronchial smooth muscle and its role in asthma and other breathing disorders is unknown in the literature. A single investigation of tracheal muscle from guinea pigs that were not sensitized to antigen identified HCN-mediated modulation of nervous system autonomic control[9]. Translational relevance of this finding to human asthma is limited by substantial differences between tracheal muscle and bronchial muscle responsible for asthmatic bronchoconstriction (see Human Trachealis and Main Bronchi Smooth Muscle Are Normoresponsive in Asthma Gijs Ijpma, Linda Kachmar, Oleg S. Matusovsky, Jason H. T. Bates, Andrea Benedetti, James G. Martin, Anne-Marie Lauzon Am J Respir Crit Care Med. 2015 Apr. 15; 191(8): 884-893; Published online 2015 Apr. 15), and direct sympathetic enervation of guinea pig airways that is not found in human lungs (see Richardson J, Beland J Nonadrenergic inhibitory nervous system in human airways. Journal of Applied Physiology 41(5 Pt1): 764-771). HCN4 function has been elucidated in the SA node of the heart, where $I_f$ current determines heart rate by influencing the rate of diastolic depolarization.[4] Associations between long acting $\beta_2$-adrenoceptor ($\beta_2$-AR) agonist use in asthma therapy and serious adverse events, together with severe asthma phenotypes that are poorly responsive to conventional asthma therapies, highlight a need for novel asthma therapeutics.[10-14] (See also Fajt M L, Wenzel S E. Development of New Therapies for Severe Asthma. Allergy Asthma Immunol Res. 2017 January; 9(1):3-14.)

SUMMARY

It is an object of the present invention to provide therapeutic compositions and methods for the prevention and/or treatment of airway obstructive disorders that involve bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof.

It is another object of the present invention to provide therapeutic compositions and methods that reduce the need, use, and/or dependence on rescue medications needed as a result of bronchial hyper-responsiveness (BHR), asthma, horse asthma, and any other airway obstructive disorders that involve bronchial smooth muscle (BSM) constriction or possibly other airway smooth muscle (ASM) constriction in a subject in need thereof.

It is a further object of the present invention to provide therapeutic compositions and methods that reduce the symptoms of bronchial hyper-responsiveness (BHR), asthma, horse asthma, and any other airway obstructive disorders that involve bronchial smooth muscle (BSM) constriction or possibly other airway smooth muscle (ASM) constriction in a subject in need thereof.

In accordance with the above stated objects and still others, the present invention provides, in part, therapeutic compositions for prevention and/or treatment of airway obstructive disorders that involve bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic compositions of the present invention comprise a therapeutically effective amount of a (benzocycloalkyl) alkylamine as active ingredient, a specific HCN4 channel blocker, which is more precisely defined herein. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride, each of which are defined more precisely herein. In some embodiments, the therapeutic composition comprising a (benzocycloalkyl) alkylamine comprises one or more further pharmaceutical active ingredients.

The present invention also provides, in part, therapeutic methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of this aspect of the present invention comprise administration of a therapeutically effective amount of a therapeutic composition comprising a (benzocycloalkyl) alkylamine as active ingredient to a subject in need thereof. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

The present invention also provides, in part, therapeutic methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of this aspect of the present invention comprise administration of a therapeutically effective amount of a therapeutic composition comprising a (benzocycloalkyl) alkylamine as active ingredient to a subject in need thereof. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

The present invention also provides, in part, therapeutic methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of this aspect of the present invention comprise administration of a therapeutically effective amount of a therapeutic composition comprising a (benzocycloalkyl) alkylamine as active ingredient to a subject in need thereof. In such embodiments, the subject in need thereof will (preferably) require a reduced amount of rescue medications as compared to a subject in need thereof who is not administered the therapeutic compositions comprising a (benzocycloalkyl) alkylamine as active ingredient. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

The present invention also provides, in part, therapeutic methods for reducing airway shear stress and oxidative stress that elicit structural changes collectively termed airway remodeling. The therapeutic methods of this aspect of the present invention comprise administration of a therapeutically effective amount of a therapeutic composition comprising a (benzocycloalkyl) alkylamine as active ingredient to a subject in need thereof. In such embodiments, the subject in need thereof will have reduced airway shear stress and oxidative stress as compared to a subject in need thereof who is not administered the therapeutic compositions comprising a (benzocycloalkyl) alkylamine as active ingredient. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for reducing airway shear stress and oxidative stress comprise the administration of a therapeutic composition comprising a (benzocycloalkyl) alkylamine as an active ingredient and further comprise one or more other pharmaceutically active ingredients. In some embodiments, the methods for reducing airway shear stress and oxidative stress comprise the administration of a therapeutic composition comprising a (benzocycloalkyl) alkylamine as an active ingredient and further comprise a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

In certain embodiments of any of the above therapeutic compositions and methods, the subject in need thereof is a mammal, especially human patients, household pets (e.g., dogs and cats), and agriculturally important domesticated animals (e.g., horses, cattle, sheep, goats, pigs, etc.). Preferably, the therapeutically effective amount of the therapeutic compositions comprising (benzocycloalkyl) alkylamine is administered in a dosage from 1 mg to 5 g, depending on the subject mammal, weight of the subject, and other dosing regimen particulars well-known in the art (e.g., nature and severity of the disorder). For a human patient, the therapeutically effective amount is preferably administered in a dosage from 1 mg to 500 mg, and from once to several times (e.g., 2, 3, 4, 5, 6, 7, etc.) per day. The circulating bioavailable serum concentration of the (benzocycloalkyl) alkylamine in some embodiments is from 1 to 100 µM, or from 1 to 50 µM, or from 1 to 25 µM. In preferred embodiments, the circulating bioavailable serum concentration of the (benzocycloalkyl) alkylamine is from 1 to 10 µM, and more preferably from 1 to 5 µM. Administration of the therapeutic compositions comprising (benzocycloalkyl) alkylamine may be effected by any appropriate route.

BRIEF DESCRIPTION OF THE DRAWINGS

Further advantages of the invention will become apparent by reference to the detailed description of preferred embodiments when considered in conjunction with the drawings:

FIGS. 1A-1I depict HCN4 protein expression increases in BSM and airway epithelium during asthma-like disease in an equine asthma model, and decreases during remission, maintaining constitutive expression in diseased BSM exceeding that of non-diseased horses. FIGS. 1A, 1B, & 1C, respectively) but exceeds non-diseased controls, and note that HCN4 staining is no longer evident in airway epithelium during disease remission.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The phrase "active ingredient" refers to an individual active substance (e.g., a (benzocycloalkyl) alkylamine HCN channel blocker) when in the context of being administered alone. More specifically, it refers to a pharmaceutical blocker of the channel activity or porosity of a HCN channel (any of HCN1, HCN2, HCN4, and combinations thereof) expressed in pulmonary tissue (especially smooth muscle tissue in the lung). When applied to a combination, the term refers to combined amounts of the "active ingredients" that result in the therapeutic effect(s) or shared therapeutic effect, whether administered in combination, serially, or simultaneously.

The phrases "administration form" and "form of administration" refer to the form of the therapeutic composition of the present invention for delivering to a subject in need thereof, and may include any suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, and other forms suitable for administration to a subject in need thereof as prescribed by a physician.

The phrase "pharmaceutically-acceptable excipients" refer to inactive ingredients well-known in the art and may depend on the form of administration, such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Depending on the desired release profile of the active(s), an administration form of the therapeutic compositions (administered in the inventive methods) of the present invention may contain a suitable amount of controlled-release agents, extended-release agents, and/or modified-release agents.

The phrase "subject in need thereof" refers to a mammal, especially human patients, household pets (e.g., dogs and cats), and agriculturally important domesticated animals (e.g., horses, cattle, sheep, goats, pigs, etc.), that suffers from or is afflicted with a breathing disorder, which may include, but is not limited to, bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction from which treating or preventing of the same; treating, reversing, and/or preventing a symptom of the same; and/or reducing the need, use, and/or dependence on rescue medications needed as a result of the same would be benefitted by such medical intervention. A subject in need thereof may also be a mammal, especially human patients, household pets (e.g., dogs and cats), and agriculturally important domesticated animals (e.g., horses, cattle, sheep, goats, pigs, etc.), who is at risk of contracting the disease or suspected to have contracted the disease as well as mammals who are ill or have been diagnosed as suffering from a disease or medical condition, and includes suppression of clinical relapse or exacerbation.

The phrase "therapeutic composition" refers to a composition suitable for pharmaceutical use comprising one or more (benzocycloalkyl) alkylamine HCN channel (any of HCN1, HCN2, HCN4, and combinations thereof) blockers and a pharmaceutically-acceptable excipient. The therapeutic composition may contain one or more additional active ingredients or be administered in combination, serially, or simultaneously with a second therapeutic composition comprising a separate active ingredient(s).

The phrase "therapeutically effective amount" refers to that amount of a substance (e.g., a therapeutic composition) that produces some desired local or systemic effect at a reasonable benefit/risk ratio applicable to any treatment. The effective amount of such substance will vary depending upon the subject and disease condition being treated, the weight and age of the subject, the severity of the disease condition, the manner of administration and the like, which can readily be determined by one of ordinary skill in the art.

The term "treatment" or "treat" or "prevent" or "reduce" or "reverse" refer to both prophylactic or preventative treatment (as the case may be) as well as curative or disease modifying treatment, including treatment of a subject in need thereof. The treatment may be administered to a subject in need thereof having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected or increase quality of life in the absence of such treatment.

Herein, we demonstrate a significant increase in HCN4 message in lung tissue during exacerbation of a spontaneous and neutrophilic asthma-like disease in horses. Increased HCN4 protein expression localizes to BSM and to a lesser extent airway epithelium during asthma-like disease and decreases during remission of asthma-like signs. The presence of HCN4 in BSM in this work indicates that $I_f$ current has a role in BSM excitability. Increased HCN4 expression in BSM during bronchospasm advances a paradigm in which changes in the magnitude of $I_f$ current contribute to BSM excitability in certain disease states, presenting a novel target for asthma therapeutics. Furthermore, the overlapping expression of HCN1, HCN2, and HCN4 in pulmonary smooth muscle does not rule out a role for these channels as well, as it should be noted that HCN channels are formed by hetero- and homo-dimers, and ivabradine is known to block all of these HCN channels.

Accordingly, in one aspect the invention relates to therapeutic compositions for preventing and/or treating bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic compositions of the present invention comprise a therapeutically effective amount of a (benzocycloalkyl) alkylamine as active ingredient, a specific HCN channel blocker.

The (benzocycloalkyl) alkylamine active ingredient may be any compound of formula (I) or (IV) of U.S. Pat. No. 5,296,482 to Peglion et al. (incorporated herein by reference in its entirety to the extent not contradictory). In preferred embodiments, the (benzocycloalkyl) alkylamine is ivabradine and its salts with a pharmaceutically-acceptable acid, especially its hydrochloride salt, as shown in U.S. Pat. Nos. 7,361,649 B2 and 7,361,650 B2 as formula (I) (both are incorporated herein by reference in their entirety to the extent not contradictory). In some embodiments, ivabradine may be selected from the forms, polymorphs, and/or salts disclosed in Publication WO 2015001569 A1 by Lykoudis et al., EP 2781509 A1 by Barreca et al., EP2471780 B1 to Singh et al., and U.S. Pat. No. 9,440,924 to Wieser et al. (each of which is incorporated herein by reference in its entirety to the extent not contradictory). More preferably, ivabradine hydrochloride is selected from the group consisting of a β-crystalline form of ivabradine hydrochloride taught in U.S. Pat. Nos. 7,361,649 B2 and 7,879,842 B2 (incorporated herein by reference in its entirety to the extent not contradictory) and a γ-crystalline form of ivabradine hydrochloride taught in U.S. Pat. Nos. 7,361,650 B2 and 7,867,996 B2 (incorporated herein by reference in its entirety to the extent not contradictory).

In some embodiments, the therapeutic composition comprising a (benzocycloalkyl) alkylamine comprises one or more further pharmaceutical active ingredients. Examples of other therapeutic agents that may be combined with a (benzocycloalkyl) alkylamine, either administered separately or in the same therapeutic compositions, include, but are not limited to: (a) VLA-4 antagonists, (b) corticosteroids, such as beclomethasone, methylprednisolone, betamethasone, prednisone, prenisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as $β_2$-agonists (e.g., terbutaline, metaproterenol, fenoterol, isoetharine, albuterol, bitolterol and pirbuterol) and β2-agonist-corticosteroid combinations (e.g., salmeterol-fluticasone (Advair®), formoterol-budesonid (Symbicort®)), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); and (i) other $PGD_2$ receptor antagonists, especially DP antagonists. When the other therapeutic agent(s) combined with a (benzocycloalkyl) alkylamine therapeutic composition of the present invention is/are administered separately, that separate composition may be administered prior to, after, or substantially simultaneously/contemporaneously to the therapeutic composition comprising a (benzocycloalkyl) alkylamine. The term "substantially simultaneously/contemporaneously" should be understood in this context to refer to a state of administration that exists when a first therapeutic composition has been administered and the active ingredient of the first therapeutic composition is still present in the subject at the same time as the administration of a second (or later) therapeutic administration. The therapeutic composition comprising a (benzocycloalkyl) alkylamine may be either the first or the second (or later) therapeutic composition in this context.

In certain embodiments of any of the above and below mentioned therapeutic compositions and methods, the subject in need thereof is a mammal, especially human patients, household pets (e.g., dogs and cats), and agriculturally important domesticated animals (e.g., horses, cattle, sheep, goats, pigs, etc.). Preferably, the therapeutically effective amount of the therapeutic compositions comprising (benzocycloalkyl) alkylamine is administered in a dosage from 1 mg to 5 g, depending on the subject mammal, weight of the subject, and other dosing regimen particulars well-known in the art (e.g., nature and severity of the disorder). For a human patient, the therapeutically effective amount is preferably administered in a dosage from 1 mg to 500 mg, and from once to several times (e.g., 2, 3, 4, 5, 6, 7, etc.) per day. The circulating bioavailable serum concentration of the (benzocycloalkyl) alkylamine in some embodiments is from 1 to 100 or from 1 to 50 or from 1 to 25 µM. In preferred embodiments, the circulating bioavailable serum concentration of the (benzocycloalkyl) alkylamine is from 1 to 10 and more preferably from 1 to 5 µM. Administration of the therapeutic compositions comprising (benzocycloalkyl) alkylamine may be effected by any appropriate route; however, an oral tablet dosage form is preferred for some embodiments. Administration by inhalation route is particularly advantageous for individuals who do not need (or it is not desired) to have cardiac rhythm modulation by the active ingredient. By introducing the active ingredient directly to the target tissue via inhalation or other direct lung route may require lower doses (e.g., less than 1 mg to 500 mg for a human subject in need thereof) and prevent heart rate decreases due to cardiac effective serum concentrations of active. Also, inhalation may allow for higher concentrations to directly treat an asthma or other breathing attack in progress.

It is important to note that the preferred method of treatment is prevention with the therapeutic compositions and methods of the present invention. Administration of the therapeutic compositions of the present invention perform best by being available to block HCN channels (any of HCN1, HCN2, and/or HCN3, and any combination thereof) in a pulmonary (lung) tissue that expresses one or more of these HCN channel proteins. Once a BSM constriction attack occurs, the effectiveness of the therapeutic compositions may be diminished for that attack event. By modulating the activity/porosity of a HCN channel in pulmonary tissue, without wishing to be bound by any particular theory of mechanism of action, the onset of a BSM constriction attack may be lessened in severity, in duration, and/or in frequency. Furthermore, airway remodeling that potentiates BHR may be lessened in subjects receiving the benefit of the therapeutic compositions and methods of the present invention.

In another aspect the invention relates to therapeutic methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of the present invention comprise administration of a therapeutically effective amount of a therapeutic composition comprising a (benzocycloalkyl) alkylamine as active ingredient to a subject in need thereof. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for prevention and/or treatment bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

In another aspect the invention relates to therapeutic methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of the present invention comprise administration of a therapeutically effective amount of a therapeutic composition comprising a (benzocycloalkyl) alkylamine as active ingredient to a subject in need thereof. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for treating, reversing, and/or preventing a symptom of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

In another aspect the invention relates to therapeutic methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction in a subject in need thereof. The therapeutic methods of the present invention comprise administration of a therapeutically effective amount of a therapeutic composition comprising a (benzocycloalkyl) alkylamine as active ingredient to a subject in need thereof. In such embodiments, the subject in need thereof will (preferably) require a reduced amount of rescue medications as compared to a subject in need thereof who is not administered the therapeutic compositions comprising a (benzocycloalkyl) alkylamine as active ingredient. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises one or more other pharmaceutically active ingredients. In some embodiments, the methods for reducing the need, use, and/or dependence on rescue medications needed as a result of bronchial hyper-responsiveness (BHR), asthma, horse asthma, airway remodeling that potentiate BHR, and any other airway obstructive disorders that involve bronchial smooth muscle (BSM) constriction or possibly other airway smooth muscle (ASM) constriction comprises the administration of a therapeutic composition comprising a (benzocycloalkyl) alkylamine as an active ingredient and further comprises a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

In another aspect the invention relates to therapeutic methods for reducing airway shear stress and oxidative stress that elicit structural changes collectively termed airway remodeling. These remodeling changes include increases in airway smooth muscle, goblet cell hyperplasia, fibrosis, changes in fibers of the elastic system, and airway inflammation which are contributing factors to airway hyper-responsiveness that are modulated by HCN channel signaling. The therapeutic methods of this aspect of the present invention comprise administration of a therapeutically effective amount of a therapeutic composition comprising a (benzocycloalkyl) alkylamine as active ingredient to a subject in need thereof. In such embodiments, the subject in need thereof will have reduced airway shear stress and oxidative stress as compared to a subject in need thereof who is not administered the therapeutic compositions comprising a (benzocycloalkyl) alkylamine as active ingredient. In preferred embodiments, the (benzocycloalkyl) alkylamine is ivabradine and its salts with a pharmaceutically-acceptable acid, especially its hydrochloride salt. More preferably, ivabradine hydrochloride is selected from the group consisting of a β-crystalline form of ivabradine hydrochloride and a γ-crystalline form of ivabradine hydrochloride. In some embodiments, the methods for reducing airway shear stress and oxidative stress comprise the administration of a therapeutic composition comprising a (benzocycloalkyl) alkylamine as an active ingredient and further comprise one or more other pharmaceutically active ingredients. In some embodiments, the methods for reducing airway shear stress and oxidative stress comprise the administration of a therapeutic composition comprising a (benzocycloalkyl) alkylamine as an active ingredient and further comprise a step of administering a pharmaceutical composition comprising one or more other pharmaceutically active ingredients. The second administration step may be performed before, during, or after the administration step comprising the (benzocycloalkyl) alkylamine-containing therapeutic composition. The second administration step, may, therefore, be substantially simultaneous/contemporaneous with, temporally near to, or temporally removed from the first administration step.

Example 1

Materials and Methods—Tissue Specimens:

Lung specimens from seven horses with a diagnosis of SPARAO and five control horses without SPARAO were used in this investigation. Diagnosis of SPARAO was based on abnormal lung function and seasonally recurring obstructive respiratory disease when exposed to pasture during summers in Louisiana or Mississippi. Signs of disease included overt respiratory distress, pronounced expiratory wheezes throughout the lung fields and fluid in the trachea upon auscultation, intermittent cough and airway neutrophilic inflammation (>10% non-degenerate neutrophils in BAL fluid). During disease remission, SPARAO-affected horses had normal bronchovesicular sounds during auscultation of the lungs with the aid of a rebreathing bag, and <10% non-degenerate neutrophils in BAL fluid. Control horses lacked evidence of respiratory disease and had <3% neutrophils in BAL fluid.

Serial lung biopsies for transcriptome analysis were acquired from two SPARAO affected and two control horses via a transthorascopic approach during seasonal disease exacerbation and remission. Animal procedures were approved by the Animal Care and Use Committee, Mississippi State University. SPARAO affected horses were Tennessee Walking Horses: an 18 year old castrated male and a 17 year old female. Control horses were castrated male American Quarter Horses aged 11 and 13. Lung biopsies were stored at −80° C. in RNA later (Ambion, Austin, Tex.).

Immunohistochemical staining was performed on archived formalin-fixed, paraffin embedded lung attained from animal procedures approved by the Animal Care and Use Committee, Louisiana State University. Tissues had been collected immediately following humane euthanasia from 3 SPARAO-affected horses (7, 16, and 19 years old) and three age-matched, non-diseased control horses that were euthanized during seasonal disease exacerbation. This diseased cohort included an Appaloosa, a Quarter Horse, and a Welsh pony, all castrated males; controls included two Quarter Horses and one American Saddlebred, one castrated male and two females. Two female SPARAO-affected horses, both Quarter Horses, 12 and 17 years of age, were euthanized during disease remission. The magnitude of neutrophilic inflammation and gross postmortem findings in the SPARAO cohort that was used for immunohistochemistry analysis has been previously correlated to disease severity and peribronchial inflammation.[17]

RNA Sequencing and Differential Expression Analysis

Total RNA was isolated from equine lung biopsies using Qiagen RNeasy Maxi protocol (Qiagen, Valencia, Calif.) per the manufacturer's instructions. Paired end sequencing of isolated RNA (RIN=7.1-9.3) was performed using Illumina TrueSeq v. 2 with Hi-Seq 2000 v. 3 chemistry (Illumina). Differential expression analysis was limited to the forward reads. Filtration and trimming were performed using FAST QC (Babraham Bioinformatics). Reads were aligned to the equine reference genome (EquCab2.1; GeneBank Assembly ID: GCF_000002305.1) with Bowtie 2[1s] and differential expression determined using ERANGE[2s].

Gene products with significant differential expression (DEGs) between seasonal exacerbation and remission at a 5% false discovery rate (FDR) were identified for each horse, sorted, and matched to identify a set of DEGs common to both affected horses and a second set of DEGs common to both control horses. From these two sets, differentially expressed gene products present in affected horses, but absent in control horses, were identified.

Immunohistochemistry

Translation of HCN4 mRNA, its differential expression in association with disease, and cellular localization were confirmed using immunohistochemistry. Lung sections were incubated at 75° C. to remove excess paraffin. Slides were placed in serial alcohol dilutions for a total of three minutes to remove excess paraffin: 100% xylene, 100% xylene, 1:1 xylene to 100% EtOH, 100% EtOH, 100% EtOH, 95% EtOH, 70% EtOH, 50% EtOH, and deionized water to rinse. Antigen retrieval was performed for 30 minutes using a vegetable steamer. Dako's target retrieval solution (Dako, North America Inc., Carpinteria, Calif., USA) was used for antigen unmasking. Slides were treated with 0.2% Triton-X100 (Sigma-Aldrich, St. Louis, Mo., USA) in TBS for 20 minutes to induce membrane permeability and blocked with Dako serum free universal protein block (Dako, Inc.). To minimize background, an avidin/biotin blocking step was performed according to manufacturer's instructions (Vector Laboratories Burlingame, Calif., USA).

Slides were incubated with rat monoclonal anti-HCN4 (Abcam ab32675; Cambridge, Mass., USA), 1:1500 for 16 hours and then treated with $H_2O_2$ for 10 minutes. A biotinylated link and streptavidin conjugated to HRP were applied for 45 minutes (LSAB+ Detection System; Dako, Inc.), followed by DAB chromogen for 10 minutes (Dako, Inc.). Slides were then counterstained with hemotoxylin for 2 minutes, dipped in 0.3% ammonia, mounted and cover slipped. Differential staining for HCN4 in lung samples was evaluated using light microscopy by a board certified veterinary pathologist (JC).

Discussion:

Translational discovery, particularly for severe and neutrophilic asthma, is challenged by commonly-employed animal asthma models, which are induced and do not adequately mirror the complexities of the human condition.[15,16] To address these challenges, herein we investigated the spontaneous equine asthma model colloquially termed 'heaves' (Recurrent Airway Obstruction, RAO)[15-17], specifically the Equine Pasture Asthma that affects horses grazing pasture during hot humid conditions. This disease has formerly been termed Summer Pasture Associated Recurrent Airway Obstruction (SPARAO)[18]. Affected horses demonstrate clinical features of asthma including reversible airway obstruction and airway hyper-responsiveness[19], chronic inflammation, and asthmatic remodeling[20,21]. Horses with Pasture Asthma exhibit seasonal exacerbation remission cycles and are clustered in the southeastern US[18]. Neutrophils rather than eosinophils predominate in the BAL fluid of affected horses[20] mimicking a population of human asthmatics that are not well-modeled by eosinophilic airway inflammation that predominates in rodent asthma models[15,16].

Genes segregating with exacerbation of a neutrophilic asthma-like disease were identified using differential expression analysis (RNA Sequencing) by comparing transcriptomes from serially sampled lung biopsies. Biopsies were collected during disease remission (winter) and at the onset of spontaneous disease exacerbation (summer) in both SPARAO-affected and non-diseased control horses. 372 gene products had seasonal differential expression conserved in diseased horses, but were not differentially expressed by season in control horses. Among these were gene products relevant to asthma, such as SAA[22,23], S100A9[24], Tbx2[25], CLCA1[26], ITGB1[27], fibroblast growth factors[28], TAK1[29], SYT1[30], supporting the translational relevance of our approach to human asthma. Based on evidence that $\beta_2$-AR signaling is necessary for the asthma phenotype in a murine model[31], and the aforementioned concerns that long-acting $\beta_2$-AR agonist use increases serious adverse effects in asthmatic patients[10-14], we sought genes with functional relevance to $\beta_2$-AR signaling that were not previously investigated in asthma to identify novel facets of asthma pathophysiology. Among these, HCN4, belonging to a gene family that regulates membrane excitability[4], was targeted based upon evidence of strong selective differential regulation directly linked to exacerbation of the equine asthma-like disease (e.g., raw read counts approaching zero during disease remission in both affected horses and in control horses with significant expression during seasonal exacerbation only in diseased horses).

Figure 1A:
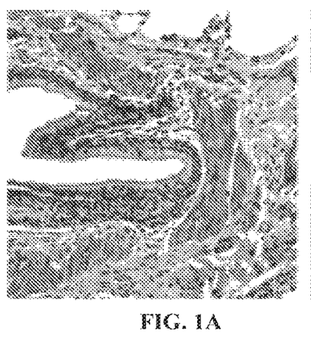
FIGS. 1A, 1B, & 1C show HCN4 stained lung sections collected during disease exacerbation from three SPARAO affected horses (1A, 1B, & 1C, ages 19, 7, and 16; respectively).
Figure 1B:
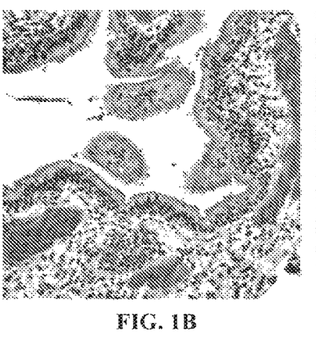
Figure 1C:
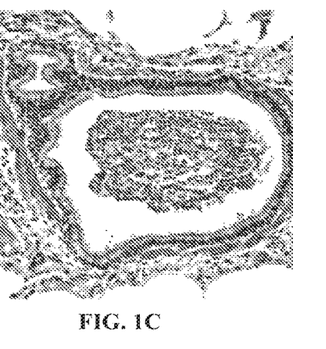
Figure 1D:
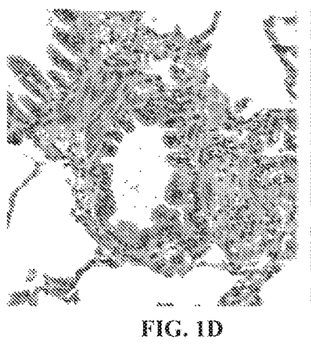
FIGS. 1D, 1E, & 1F show HCN4 stained lung sections of respective age and season matched lung sections from non-diseased control horses relative to those shown in FIGS. 1A, 1B, & 1C, respectively, demonstrate strong HCN4 staining in BSM and to a lesser extent in the apical regions of epithelial cells during disease. In panels FIGS. 1G, 1H, & 1I HCN4 stained lung sections collected during disease remission identify constitutive HCN4 staining in BSM that is less than observed during disease exacerbation (cf.
Figure 1E:
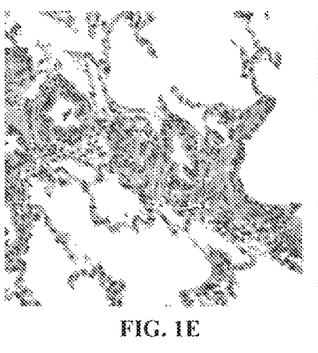
Figure 1F:
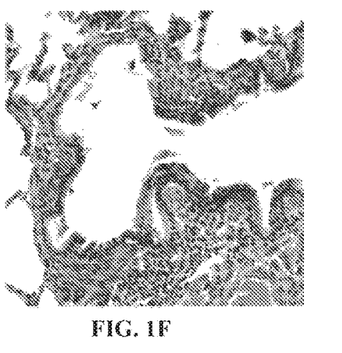
Figure 1G:
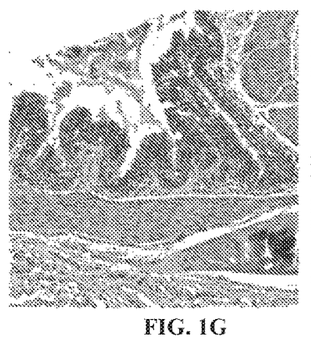
Figure 1H:
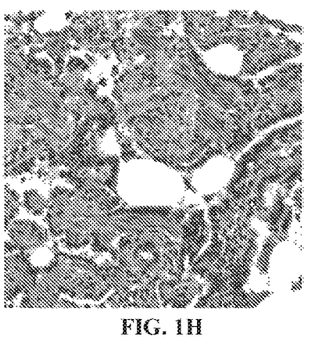
Figure 1I:
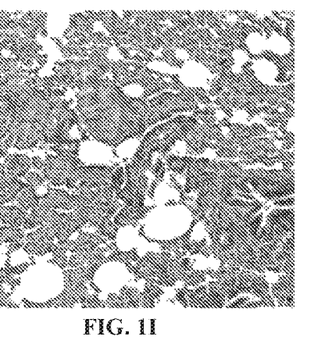

Though there is evidence of HCN4 transcription in human lung expression databases[32,33], evidence of HCN4 translation in the lung and its cellular location are absent. To confirm increased HCN4 expression at the protein level in our asthma model, and to localize its cellular expression, HCN4 protein was stained in archival lung tissues collected from an unrelated cohort of diseased and age matched control horses. Immunohistochemical staining confirmed strong HCN4 protein expression in BSM, and to a lesser extent in airway epithelium during disease exacerbation (FIGS. 1A-1C), contrasting non-diseased age matched control lung harvested during seasonal disease exacerbation in which HCN4 staining was not identified (FIGS. 1D-1F). In lung harvested from diseased horses during seasonal disease remission, HCN4 staining remained evident but was reduced in BSM and was rare in bronchial epithelium (FIGS. 1G-1I) in comparison to HCN4 staining during clinical disease (FIGS. 1A-1C). HCN4 staining in BSM of diseased horses during remission (FIGS. 1G-1I) was clearly greater than the baseline of expression demonstrated by control horses (FIGS. 1D-1F).

HCN channels, as reviewed by Postea[4], are six transmembrane domain, single pore-loop cation channels capable of activation by membrane hyperpolarization or cyclic nucleotide (cAMP) binding. Four HCN isoforms (HCN1-4) are characterized with differing tissue distributions, activation kinetics, and cAMP sensitivity. The resulting cation current is termed funny current ($I_f$) because channel opening is activated by membrane hyperpolarization at the negative cellular voltage extremes that follow action potentials, a reverse of the voltage dependence that characterizes most ion channels. In this manner, HCN channels provide excitable tissues the unique ability to depolarize without external influences through sustained positive increases in membrane potential that are initiated by hyperpolarization and raise the membrane potential to the threshold for subsequent depolarization. This characteristic contributes to membrane responsiveness and makes funny current a pacemaker of rhythmic nerve and muscle firing. Accordingly, in the heart, the magnitude of funny current resulting from HCN4 channel activation regulates the slope (duration) of phase 4 diastolic depolarization; determining the frequency of spontaneous action potential firing of SA myocytes and therefore heart rate. The specific HCN4 channel blocker ivabradine, binds to an intracellular site in the HCN4 channel pore, inhibiting $I_f$ current, which blunts the diastolic depolarization rate and decreases heart rate.[34] Without being bound by any particular theory, HCN channel blockers are useful for treating and/or preventing asthma, and other breathing disorders by preventing or lessening contraction of airway smooth muscle or by decreasing sheer stress dependent inflammation of airway smooth muscles in asthmatic subjects or others with inflammation-based or associated breathing disorders. It is believed that at least a portion of the beneficial therapeutic effects from HCN channel blockade by a therapeutic composition of the present invention moderates shear induced inflammatory cascades important in airway contraction.

Cyclic nucleotide gating makes HCN channels also responsive to the autonomic nervous system[4]. HCN4 channels, which co-localize with $B_2$-AR in the heart[35], are slowly gating and strongly sensitive to cAMP. cAMP binds directly to f-channels and shifts the $I_f$ activation range to more positive voltages, increasing $I_f$ channel opening probability. In the heart, this increases the steepness of diastolic depolarization, shortening its duration and causing heart rate acceleration. Autonomic regulation of heart rate is accordingly achieved by increases or depletion of cAMP that result from β-adrenergic or muscarinic M2 receptor stimulation, respectively. Recently, cyclic dinucleotides have been demonstrated to inhibit HCN4 opening, mimicking the effects of muscarinic $I_f$ modulation and providing a mechanism for crosstalk with the immune system where cNDP signaling is well recognized.[36]

In light of evidence that HCN channels modulate excitability in cardiac and smooth muscle, our observations of constitutive expression of HCN4 protein in association with BSM during remission, followed by a sharp increase in BSM and in epithelium during disease, illustrate a need to define the role of $I_f$ current in BSM excitability and contraction in asthma. One potential scenario is that HCN4 mediated $I_f$ current raises BSM membrane potential to thresholds that activate voltage gated calcium channels, providing an alternate route of excitation to the GPCR-IP$_3$-mediated $Ca^{+2}$ release from SR that predominates in BSM contraction. Myometrium, which shares this primary contractile pathway with BSM and has a parallel dependence on intracellular Ca2+ stores for contraction, exhibits changes in the calcium machinery of the gravid rat uterus that support this hypothesis. Hyperpolarization-activated inward currents are identified in advancing pregnancy in rat myometrium[32] and both L-type and T-type voltage gated Ca2+ channels[38] as well as gap junctions[39] increase in gravid myometrium with advancing gestation. The resulting current contributes to maintenance of the resting membrane potential and spontaneous activity in smooth muscle cells of late pregnant rats.[37] $I_f$ current in BSM also indicates a mechanistic explanation for the paradoxical ability of $β_2$-AR agonists to mediate bronchodilation in most asthmatic patients, while simultaneously effecting bronchoconstriction in more severe asthmatics. Specifically, while $β_2$-AR agonist mediated increases in cAMP drive BSM relaxation through PKC signaling and downstream effects on MLC-20, cAMP gating simultaneously increases HCN4 channel opening, facilitating BSM contraction via a depolarizing shift in the BSM membrane potential. The outcome of $β_2$-AR signaling thus reflect the balance between PKC driven BSM relaxation and HCN4 driven BSM contraction. From this line of evidence emerges the hypothesis that $I_f$ modulation may be of value in changing BSM responsiveness in certain populations of asthmatics.

Overall, this demonstrates the first preferential transcription and translation of HCN4 in association with BSM in an asthma model. Interpreted with the documented role of HCN4 in regulating membrane excitability, these findings show a role for $I_f$ current in BSM in asthma and provide new roles of HCN4 in airway hyper-responsiveness and bronchoconstriction, and as a therapeutic target for $I_f$ modulation in managing selected asthma populations. Due to the overlapping expression of HCN1, HCN2, and HCN4 in pulmonary smooth muscle tissue, therapeutic blockade of HCN4 and any of the other HCN channels in pulmonary tissue provides a novel treatment option for subjects suffering from breathing disorders.

ENUMERATED REFERENCES

1. Barnes P J. Pathogenesis of asthma: a review. *J R Soc Med.* 76, 580-586 (1983). PMID: 6308253
2. Crapo, R. O. et al. Guidelines for methacholine and exercise challenge testing-1999. This official statement of the American Thoracic Society was adopted by the ATS Board of Directors, July 1999. *Am J Respir Crit Care Med.* 161, 309-329 (2000). PMID: 10619836
3. Sont, J. K. et al. Clinical control and histopathologic outcome of asthma when using airway hyperresponsiveness as an additional guide to long-term treatment. The AMPUL Study Group. *Am J Respir Crit Care Med.* 159, 1043-1051 (1999). PMID:24189942
4. Postea, O. & Biel, M. Exploring HCN channels as novel drug targets. *Nat Rev Drug Discov.* 10, 903-914 (2011) PMID:22094868
5. Xue, L. et al. Investigation of hyperpolarization-activated cyclic nucleotide-gated channels in interstitial cells of Cajal of human bladder. *Urology.* 80, 224.e13-224.e18 (2102). PMID: 22748890
6. Xiao, J. et al. Molecular and functional analysis of hyperpolarisation-activated nucleotide-gated (HCN) channels in the enteric nervous system. *Neuroscience.* 129, 603-614 (2004). PMID:15541882
7. Hurtado, R., Bub, G. & Herzlinger, D. A molecular signature of tissues with pacemaker activity in the heart and upper urinary tract involves coexpressed hyperpolarization-activated cation and T-type $Ca^{2+}$ channels. *FASEB J.* 28, 730-739 (2014). PMID: 24189942
8. Greenwood, I. A. & Prestwich, S. A. Characteristics of hyperpolarization-activated cation currents in portal vein smooth muscle cells. *Am J Physiol Cell Physiol* 282, C744-C753 (2002). PMID: 11880262
9. McGovern, A. E. et al. The effect of hyperpolarization-activated cyclic nucleotide-gated ion channel inhibitors on the vagal control of guinea pig airway smooth muscle tone. *Br J Pharmacol.* 171, 3633-3650 (2014). PMID: 24762027
10. Nelson, H. S. et al. The Salmeterol Multicenter Asthma Research Trial: a comparison of usual pharmacotherapy for asthma or usual pharmacotherapy plus salmeterol. *Chest* 129, 15-26 (2006). PMID:16424409
11. Salpeter S R, Buckley N S, Ormiston T M, Salpeter E E. Meta-analysis: effect of long-acting beta-agonists on severe asthma exacerbations and asthma-related deaths. *Ann Intern Med.* 144, 904-912 (2006). PMID: 16754916
12. Salpeter S R. An update on the safety of long-acting beta-agonists in asthma patients using inhaled corticosteroids. *Expert Opin Drug Saf* 9, 407-419 (2010). PMID: 20408768
13. Cates, C. J. & Cates, M. J. Regular treatment with formoterol for chronic asthma: serious adverse events. *Cochrane Database Syst Rev.* 18, CD006923 (2012). PMID:22513944
14. Cates C J, Wieland L S, Oleszczuk M, Kew K M. Safety of regular formoterol or salmeterol in adults with asthma: an overview of Cochrane reviews. *Cochrane Database Syst Rev.* 2014 2, CD010314 (2014). PMID: 24504983
15. Kirschvink, N. & Reinhold, P. Use of alternative animals as asthma models. *Current drug targets* 9, 470-484 (2008).
16. Zosky, G. R. & Sly, P. D. Animal models of asthma. Clinical and experimental allergy: journal of the British Society for Allergy and Clinical Immunology 37, 973-988 (2007).
17. Leclere, M., Lavoie-Lamoureux, A. & Lavoie, J. P. Heaves, an asthma-like disease of horses. *Respirology (Carlton, Vic)* 16, 1027-1046 (2011). PMID21824219
18. Costa, L. R., Johnson, J. R., Baur, M. E. & Beadle, R. E. Temporal clinical exacerbation of summer pasture-associated recurrent airway obstruction and relationship with climate and aeroallergens in horses. *Am J Vet Res* 67, 1635-1642 (2006). PMID 16948614,
19. Hunter, C. L. et al. Horses with a spontaneous, non-eosinophilic asthma-like disease demonstrate reversible airway hyper-responsiveness at methacholine doses used to diagnose moderate to severe human asthma. *Am J Respir Crit Care Med* 187, A6080 (2013).
20. Costa, L. R. et al. Correlation of clinical score, intrapleural pressure, cytologic findings of bronchoalveolar fluid, and histopathologic lesions of pulmonary tissue in horses with summer pasture-associated obstructive pulmonary disease. *Am J Vet Res* 61, 167-173 (2000).
21. Mujahid, N. et al. Smooth muscle remodeling is a histologic feature of airway remodeling in summer pasture associated recurrent airway obstruction. *J Equine Vet Sci* 31, 230-356 (2011).
22. Ather, J. L. et al. Serum amyloid A activates the NLRP3 inflammasome and promotes Th17 allergic asthma in mice. *J Immunol.* 2011 Jul. 1; 187(1):64-73 (2011)
23. Poynter M E. Airway epithelial regulation of allergic sensitization in asthma. *Pulm Pharmacol Ther.* 2012 December; 25(6):438-46. (2012)
24. Wang C H, et al. Fibrocyte trafficking in patients with chronic obstructive asthma and during an acute asthma exacerbation. *J Allergy Clin Immunol.* 2015 May; 135(5): 1154-62 (2014)
25. Tantisira K G, et al. Genome-wide association identifies the T gene as a novel asthma pharmacogenetic locus. *Am J Respir Crit Care Med.* 2012 Jun. 15; 185(12):1286-91. (2012)
26. Woodruff P G, et al. Genome-wide profiling identifies epithelial cell genes associated with asthma and with treatment response to corticosteroids. *Proc Natl Acad Sci USA.* 2007 Oct. 2; 104(40):15858-63. (2007)
27. Nguyen, T. T., Ward, J. P. & Hirst, S. J. Beta1-integrins mediate enhancement of airway smooth muscle proliferation by collagen and fibronectin. Am J Respir Crit Care Med. 171, 217-223 (2005). PMID: 15502110
28. Hoshino, M., Nakamura, Y. & Sim, J. J. Expression of growth factors and remodeling of the airway wall in bronchial asthma. *Thorax* 53, 21-27 (1998). PMID9577517
29. Pera, T., Sami, R., Zaagsma, J. & Meurs, H. TAK1 plays a major role in growth factor-induced phenotypic modulation of airway smooth muscle. *Am J Physiol Lung Cell Mol Physiol* 301, L822-828 (2011). PMID: 21873447
30. Evans, C. M., Kim, K., Tuvim, M. J. & Dickey, B. F. Mucus hypersecretion in asthma: causes and effects. *Curr Opin Pulm Med.* 15, 4-11 (2009).
31. Nguyen, L. P. et al. Beta2-adrenoceptor signaling is required for the development of an asthma phenotype in a murine model. *Proc Natl Acad Sci* 106, 2435-2440 (2009).
32. Wu, C. et al. BioGPS: an extensible and customizable portal for querying and organizing gene annotation resources. *Genome Biol* 10, R130. (2009). www.biogps.org
33. Edgar, R., Domrachev, M. & Lash, A. E. Gene Expression Omnibus: NCBI gene expression and hybridization array data repository *Nucleic Acids Res.* 30, 207-210 (2002).

34. Fox, K. et al. Ivabradine for patients with stable coronary artery disease and left-ventricular systolic dysfunction (BEAUTIFUL): a randomised, double-blind, placebo-controlled trial. *Lancet.* 372, 807-816 (2008).

35. Greene, D., Kang, S., Kosenko, A. & Hoshi, N. Adrenergic regulation of HCN4 channel requires protein association with β2-adrenergic receptor. *J Biol Chem.* 287, 23690-23697 (2012).

36. Haitin, Y. Structural biology: a 'funny' cyclic dinucleotide receptor. *Nat Chem Biol* 10, 413-414 (2014). PMID: 24838168

37. Okabe, K., et al. Physiological significance of hyperpolarization-activated inward currents (Ih) in smooth muscle cells from the circular layers of pregnant rat myometrium. *Pflugers Arch.* 439, 76-85 (1999). PMID: 10651003

38. Ohkubo, T., Kawarabayashi, T., Inoue, Y. & Kitamura, K. Differential expression of L- and T-type calcium channels between longitudinal and circular muscles of the rat myometrium during pregnancy. *Gynecol Obstet Invest* 59, 80-85 (2005). PMID:15564792

39. Orsino, A., Taylor, C. V., Lye, S. J. Connexin-26 and connexin-43 are differentially expressed and regulated in the rat myometrium throughout late pregnancy and with the onset of labor *Endocrinology* 137, 1545-1553 (1996). PMID: 8612484

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A method of reducing the need, use, and/or dependence on rescue medications needed as a result of a breathing disorder selected from the group consisting of bronchial hyper-responsiveness (BHR), asthma, equine pasture asthma, airway remodeling that potentiates BHR, bronchial smooth muscle (BSM) constriction and airway smooth muscle (ASM) constriction in a subject in need thereof comprising administering an effective amount of a therapeutic composition comprising a (benzocycloalkyl) alkylamine to the subject in need thereof during remission and blocking at least one HCN channel in pulmonary tissue.

2. The method of claim 1, wherein the (benzocycloalkyl) alkylamine is ivabradine hydrochloride.

3. The method of claim 1, wherein the (benzocycloalkyl) alkylamine is a β-crystalline form of ivabradine hydrochloride.

4. The method of claim 1, wherein the (benzocycloalkyl) alkylamine is a γ-crystalline form of ivabradine hydrochloride.

5. The method of claim 1, wherein the subject in need thereof is a mammal.

6. The method of claim 5, wherein the mammal is selected from a human, a horse, a cow, a sheep, a goat, a pig, a dog, a cat, a rat, and a mouse.

7. The method of claim 5, wherein the mammal is a human.

8. The method of claim 5, wherein the mammal is a horse.

9. The method of claim 1, wherein the step of administering a therapeutic composition further comprises administering at least a second active ingredient selected from the group consisting of: (a) VLA-4 antagonists, (b) corticosteroids, such as beclomethasone, methylprednisolone, betamethasone, prednisone, prenisolone, dexamethasone, fluticasone and hydrocortisone, and corticosteroid analogs such as budesonide; (c) immunosuppressants such as cyclosporine (cyclosporine A), tacrolimus (FK-506), rapamycin (sirolimus) and other FK-506 type immunosuppressants, and mycophenolate, e.g., mycophenolate mofetil; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol) and β2-agonist-corticosteroid combinations (e.g., salmeterol-fluticasone, formoterol-budesonid), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib and d rofecoxib; (h) inhibitors of phosphodiesterase type IV (PDE-IV); and (i) other PGD2 receptor antagonists, especially DP antagonists.

10. The method of claim 9, wherein the second active ingredient is administered before administering the (benzocycloalkyl) alkylamine.

11. The method of claim 9, wherein the second active ingredient is administered during administering the (benzocycloalkyl) alkylamine.

12. The method of claim 9, wherein the second active ingredient is administered after administering the (benzocycloalkyl) alkylamine.

* * * * *